US011452758B2

(12) United States Patent
Park et al.

(10) Patent No.: US 11,452,758 B2
(45) Date of Patent: Sep. 27, 2022

(54) ANTIMICROBIAL PEPTIDE DERIVED FROM LL37 PEPTIDE AND USES THEREOF

(71) Applicant: INDUSTRY-ACADEMIC COOPERATION FOUNDATION, CHOSUN UNIVERSITY, Gwangju (KR)

(72) Inventors: Yoonkyung Park, Jeollanam-do (KR); Eunji Park, Gwangju (KR)

(73) Assignee: INDUSTRY-ACADEMIC COOPERATION FOUNDATION, CHOSUN UNIVERSITY, Gwangju (KR)

( * ) Notice: Subject to any disclaimer, the term of this patent is extended or adjusted under 35 U.S.C. 154(b) by 0 days.

(21) Appl. No.: 16/978,387

(22) PCT Filed: Mar. 7, 2019

(86) PCT No.: PCT/KR2019/002633
§ 371 (c)(1),
(2) Date: Sep. 4, 2020

(87) PCT Pub. No.: WO2019/172666
PCT Pub. Date: Sep. 12, 2019

(65) Prior Publication Data
US 2021/0052696 A1   Feb. 25, 2021

(30) Foreign Application Priority Data
Mar. 7, 2018   (KR) .................. 10-2018-0026778

(51) Int. Cl.
| | |
|---|---|
| A61K 38/16 | (2006.01) |
| A01N 37/46 | (2006.01) |
| A23K 20/147 | (2016.01) |
| A23L 33/18 | (2016.01) |
| A61K 8/64 | (2006.01) |
| A61Q 17/00 | (2006.01) |

(52) U.S. Cl.
CPC ............. *A61K 38/16* (2013.01); *A01N 37/46* (2013.01); *A23K 20/147* (2016.05); *A23L 33/18* (2016.08); *A61K 8/64* (2013.01); *A61Q 17/005* (2013.01)

(58) Field of Classification Search
CPC ... A23K 20/147; A23K 20/195; A23L 33/135; A23L 33/18; A23L 3/34635; A23L 3/3526; A61K 38/00; A61K 38/16; A61K 8/64; A61P 31/04; A61Q 17/005; A61Q 19/00; C07K 7/08
See application file for complete search history.

(56) References Cited

U.S. PATENT DOCUMENTS

| | | |
|---|---|---|
| 2010/0048480 A1 | 2/2010 | Bommarius et al. |
| 2013/0109616 A1* | 5/2013 | Eldridge ............ C12N 15/1075 514/2.8 |

FOREIGN PATENT DOCUMENTS

| | | |
|---|---|---|
| KR | 10-1420849 B1 | 7/2014 |
| KR | 10-2018-0000531 A | 1/2018 |

OTHER PUBLICATIONS

Yu Luo, The Naturally Occurring Host Defense Peptide, LL-37, and Its Truncated Mimetics KE-18 and KR-12 Have Selected Biocidal and *Escherichia coli* In vitro, Frontiers in Microbiolog, Mar. 2017, pp. 1-11.*
Yong Hai Nan, Prokaryotic selectivity and LPS-neutralizing activity of short antimicrobial peptides designed from the human antimicrobial peptide LL-37, Peptides 35 (2012) 239-247.*
Marissa H. Braff, Structure-Function Relationships among Human Cathelicidin Peptides: Dissociation of Antimicrobial Properties from Host Immunostimulatory Activities, J Immunol Apr. 1, 2005, 174 (7) 4271-4278.*
International Search Report for PCT/KR2019/002633 dated Jun. 19, 2019.
Nell, Maija J. et al., "Development of novel LL-37 derived antimicrobial peptides with LPS and LTA neutralizing and antimicrobial activities for therapeutic application", peptides, vol. 27, pp. 649-660, 2006.
Nagaoka I. et al.,"Augmentation of the Lipopolysaccharide-Neutralizing Activities of Human Cathelicidin CAP18/LL-37-Derived Antimicrobial Peptides by Replacement with Hydrophobic and Cationic Amino Acid Residues", Clinical and Diagnostic Laboratory Immunology, vol. 9 (5), pp. 972-982, 2002.
I. Nagaoka et al., "Augmentation of the bactericidal activities of human cathelicidin CAP18/LL-37-derived antimicrobial peptides by amino acid substitutions", Inflammation Research, vol. 54, pp. 66-73, 2005.
Yijie Guo et al., "Antimicrobial and Antibiofilm Activity of Human Cationic Antibacterial Peptide (LL-37) and Its Analogs Against Pan-Drug-Resistant Acinetobacter baumannii", Jundishapur J Microbiol., vol. 10(3), pp. 1-17, 2017.
Merrifield, R.B., "Solid Phase Peptide Synthesis. I. The Synthesis of a Tetrapeptide", J. Am. Chem. Soc., vol. 85, 2149-2154, 1963.
James A. Hill, et al., "Matrix-assisted Laser Desorption Ionizationwith a magnetic Mass Spectrometer", Rapid Commun. Mass Spectrometry, vol. 5, pp. 395-399, 1991.

* cited by examiner

*Primary Examiner* — Julie Ha
*Assistant Examiner* — Erinne R Dabkowski
(74) *Attorney, Agent, or Firm* — The PL Law Group, PLLC

(57) ABSTRACT

A novel antimicrobial peptide derived from LL37 peptide has not only an excellent antimicrobial activity for Gram-positive bacteria, Gram-negative bacteria, and antibiotic tolerant bacteria but also low cytotoxicity for cells derived from mouse or human. It can be advantageously used as an effective component of antimicrobial antibiotics, cosmetic composition, food additive, animal feed additive, biopesticides, and quasi-drug.

7 Claims, 5 Drawing Sheets
Specification includes a Sequence Listing.

SEQUENCE LISTING

```
<160> NUMBER OF SEQ ID NOS: 5

<210> SEQ ID NO 1
<211> LENGTH: 37
<212> TYPE: PRT
<213> ORGANISM: Artificial Sequence
<220> FEATURE:
<223> OTHER INFORMATION: LL37

<400> SEQUENCE: 1

Leu Leu Gly Asp Phe Phe Arg Lys Ser Lys Glu Lys Ile Gly Lys Glu
1               5                   10                  15

Phe Lys Arg Ile Val Gln Arg Ile Lys Asp Phe Leu Arg Asn Leu Val
            20                  25                  30

Pro Arg Thr Glu Ser
            35

<210> SEQ ID NO 2
<211> LENGTH: 16
```

```
<212> TYPE: PRT
<213> ORGANISM: Artificial Sequence
<220> FEATURE:
<223> OTHER INFORMATION: LL37-1 peptide

<400> SEQUENCE: 2

Lys Glu Phe Lys Arg Ile Val Gln Arg Ile Lys Asp Phe Leu Arg Asn
1               5                   10                  15

<210> SEQ ID NO 3
<211> LENGTH: 16
<212> TYPE: PRT
<213> ORGANISM: Artificial Sequence
<220> FEATURE:
<223> OTHER INFORMATION: LL37-2 peptide

<400> SEQUENCE: 3

Lys Lys Phe Lys Arg Ile Val Gln Arg Ile Lys Asp Phe Leu Arg Asn
1               5                   10                  15

<210> SEQ ID NO 4
<211> LENGTH: 16
<212> TYPE: PRT
<213> ORGANISM: Artificial Sequence
<220> FEATURE:
<223> OTHER INFORMATION: LL37-3 peptide

<400> SEQUENCE: 4

Lys Glu Phe Lys Arg Ile Val Gln Arg Ile Lys Lys Phe Leu Arg Asn
1               5                   10                  15

<210> SEQ ID NO 5
<211> LENGTH: 16
<212> TYPE: PRT
<213> ORGANISM: Artificial Sequence
<220> FEATURE:
<223> OTHER INFORMATION: LL37-4 peptide

<400> SEQUENCE: 5

Lys Lys Phe Lys Arg Ile Val Gln Arg Ile Lys Lys Phe Leu Arg Asn
1               5                   10                  15
```

ANTIMICROBIAL PEPTIDE DERIVED FROM LL37 PEPTIDE AND USES THEREOF

CROSS REFERENCE TO RELATED APPLICATIONS AND CLAIM OF PRIORITY

This application claims benefit under 35 U.S.C. 119(e), 120, 121, or 365(c), and is a National Stage entry from International Application No. PCT/KR2019/002633, filed Mar. 7, 2019, which claims priority to the benefit of Korean Patent Application No. 10-2018-0026778 filed in the Korean Intellectual Property Office on Mar. 7, 2018, the entire contents of which are incorporated herein by reference.

TECHNICAL FIELD

The present invention relates to a novel antimicrobial peptide derived from LL37 peptide and uses thereof.

BACKGROUND ART

Bacterial infection is one of the most common and deadly causes of a human disease. Unfortunately, due to abuse of antibiotics, bacterial resistance to antibiotics has been yielded. The rate of exhibiting resistance to antibiotics by bacteria is indeed much faster than the rate of developing new homologues of the antibiotics. For example, various bacterial species like *Enterococcus faecalis, Acinetobacter baumannii*, and *Pseudomonas aeruginosa*, which may pose a threat to human life, have developed resistance to all antibiotics that are known until now.

Antibiotic tolerance is a phenomenon that is distinguished from the resistance to antibiotics, and after being found first in *Pneumococcus* sp. in 1970s, it provides an important clue for studying the working mechanism of penicillin. Bacterial species exhibiting the tolerance show growth stall in the presence of antibiotics at common concentration, but without any death. The tolerance is caused due to a lack of the activity of an autolytic bacterial enzyme like autolysin as the antibiotics inhibit an enzyme for synthesizing cell wall, and this leads to the results that, as an endogenous hydrolytic enzyme is activated by penicillin, bacterial cell death is caused, and the bacteria also suppress the enzyme activity to survive even under a treatment with antibiotics.

Having bacterial tolerance to various antibiotics is clinically very important because, once it becomes impossible to eradicate bacteria with tolerance, usefulness of a clinical treatment with antibiotics for infection is impaired. Furthermore, having tolerance is believed to a prerequisite requirement for developing resistance to antibiotics, and that is because there are bacterial strains which manage to survive even after a treatment with antibiotics. By acquiring new genetic elements to exhibit resistance to antibiotics, those bacterial strains keep growing even in the presence of the antibiotics. Since all bacteria exhibiting resistance are indeed known to have tolerance too, it is necessary to develop novel antibiotics which can be used for eradicating those bacteria having resistance to antibiotics.

In terms of working mechanism, the tolerance to antibiotics broadly consists of two pathways. The first pathway is phenotypic tolerance which occurs during every bacteria growth with decreasing rate, and the second pathway is genetic tolerance caused by mutation which occurs in specific types of bacteria. In all of those cases, the basic phenomenon is an occurrence of down regulation of autolysin activity. This down regulation is transient in case of phenotypic tolerance against external stimulation, while it is permanent in case of genetic tolerance in which a mutation for causing a change in pathway for regulating cell lysis occurs. The simplest genetic tolerance is based on a defect in autolysin enzyme, and due to various kinds of reasons which have not been clarified, a bacterial strain having the tolerance as caused by a defect in suicidal enzyme has not been clinically found yet, and clinical tolerance is rather achieved via regulation of the activity of autolysin.

As discussed in the above, in order to deal with bacteria which exhibit resistance to antibiotics, development of new antibiotics is necessary, and also development of new antibiotics which work independently of the activity of autolysin is required.

Meanwhile, by synthesizing peptides or small organic molecules, bacteria may kill neighboring bacteria, and, in terms of the structure, those bacteriocins are categorized into three classes. First class is lantibiotics, second class is nonlantibiotics, and third class is those secreted by signal peptides. Animals including insects also produce peptide antibiotics that are naturally produced, and those antibiotics are categorized into three groups based on their structure. First group is cysteine-rich β-sheet peptides, second group is α-helical amphipathic molecules, and third group is proline-rich peptides. Those antibiotic peptides are known to play an important role in host defense and innate immune system. Those antibiotic peptides have various structures depending on their amino acid sequence, and among those structures, LL37 (cathelicidin antimicrobial peptide) as an antimicrobial peptide found in human forms an amphipathic α-helical structure.

Meanwhile, in Korean Patent Application Publication No. 2018-0000531, "Antimicrobial peptides having high synergistic effect with antibiotics against multidrug resistant Gram-negative bacteria and their uses" is disclosed, in which the antimicrobial peptides are produced based on linkage between the residues of two antibiotic peptides, i.e., linkage between the N-terminal residue of papiliocin and the N-terminal residue of magainin, and, in Korean Patent Registration No. 1420849, "Protaetiamycine antibiotic peptide analogues exhibiting high antimicrobial activity against multidrug resistant bacteria and their uses" is disclosed. However, the novel antimicrobial peptide derived from LL37 and uses thereof as described in the present invention have never been disclosed before.

SUMMARY

The present invention is devised under the circumstances described above.

Specifically, by using as a template the amphiphilic LL37 antimicrobial peptide which has been previously reported to have an antimicrobial activity, the inventors of the present invention synthesized four novel types of LL37 homologues (i.e., LL37-1, LL37-2, LL37-3, and LL37-4) that are represented by SEQ ID NO: 2 to SEQ ID NO: 5, respectively, and, as a result of analyzing the antimicrobial activity and cytotoxicity for Gram-positive bacteria, Gram-negative bacteria, and antibiotic tolerant bacteria, the inventors found that LL37-2 and LL37-4 peptides exhibit the antimicrobial activity that is in similar or higher level than the LL37 antimicrobial peptide while showing low cytotoxicity for mouse erythrocytes and a normal human cell line. The present invention is completed accordingly.

In order to solve the problems described above, the present invention provides an antimicrobial peptide in which, in the amino acid sequence of SEQ ID NO: 1, i) the 1$^{st}$ to the 14$^{th}$ amino acids and the 31$^{st}$ to the 37$^{th}$ amino acids are deleted, and ii) the 16$^{th}$ amino acid is substituted with lysine (K), or the 16$^{th}$ and the 26$^{th}$ amino acids are substituted with lysine (K).

The present invention further provides antibiotics comprising the aforementioned antimicrobial peptide as an effective component.

The present invention further provides an antibiotic cosmetic composition comprising the aforementioned antimicrobial peptide as an effective component.

The present invention further provides an antibiotic food additive comprising the aforementioned antimicrobial peptide as an effective component.

The present invention further provides an antibiotic animal feed additive comprising the aforementioned antimicrobial peptide as an effective component.

The present invention further provides antibiotic biopesticides comprising the aforementioned antimicrobial peptide as an effective component.

The present invention further provides an antibiotic quasi-drug composition comprising the aforementioned antimicrobial peptide as an effective component.

The present invention still further provides a method for antimicrobial treatment in an individual except human including administering a pharmaceutically effective amount of the aforementioned antimicrobial peptide to an individual except human.

As the novel antimicrobial peptides (LL37-2 and LL37-4) of the present invention have not only an excellent antimicrobial activity but also low cytotoxicity, they can be advantageously used as an effective component of antimicrobial antibiotics, cosmetic composition, food additive, animal feed additive, biopesticides, quasi-drug, and the like.

DETAILED DESCRIPTION

Figure 1:
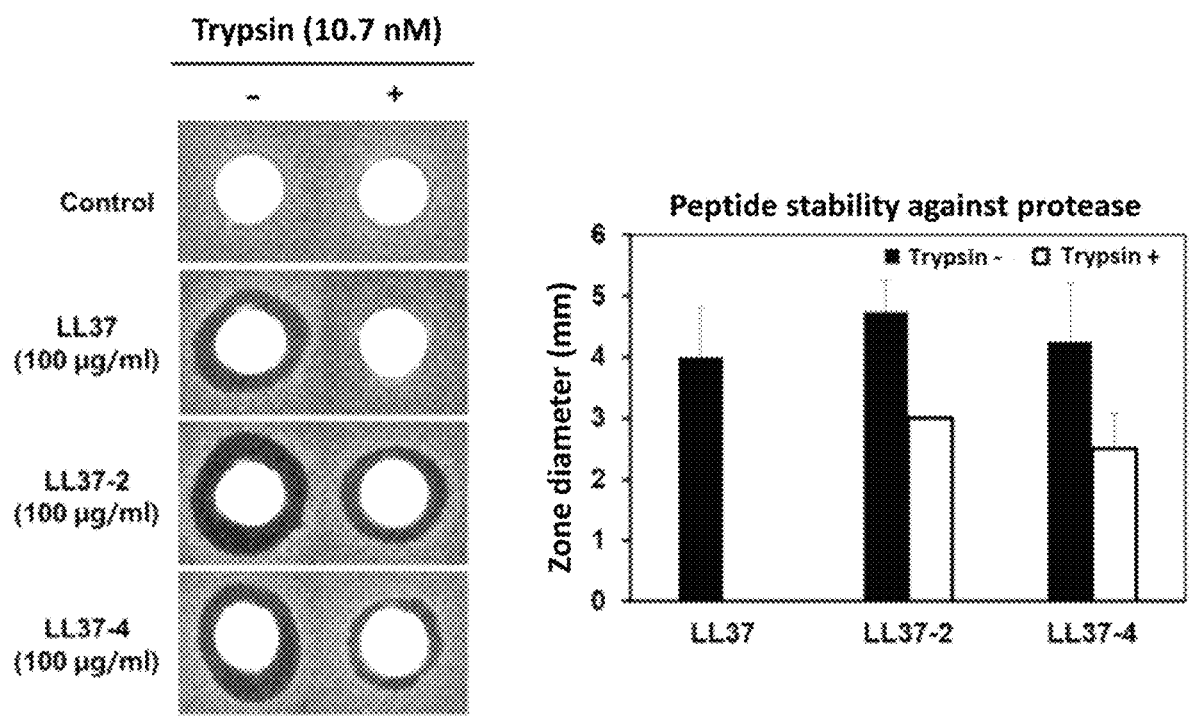
FIG. 1 shows the result to see whether or not LL37 (control) as a mother antimicrobial peptide and LL37-2 or LL37-4, which is a LL37 homologous novel peptide, stably exhibit the antimicrobial activity against *Acinetobacter baumannii* KCTC 2508 strain in the presence of trypsin as protease.

To achieve the purpose of the present invention, the present invention provides an antimicrobial peptide in which, in the amino acid sequence of SEQ ID NO: 1, i) the 1$^{st}$ to the 14$^{th}$ amino acids and the 31$^{st}$ to the 37$^{th}$ amino acids are deleted, and ii) the 16$^{th}$ amino acid is substituted with lysine (K), or iii) the 16$^{th}$ and the 26$^{th}$ amino acids are substituted with lysine (K).

LL37 peptide as a mother peptide having the previously known amino acid sequence of SEQ ID NO: 1 is cathelicidin peptide derived from human, and it is known to be an antimicrobial peptide. LL37 peptide can be produced by a method for synthesizing peptide that is well known in the pertinent art, and the production method is not particularly limited. As for the method for synthesis, synthesis is preferably carried out according to a method for chemical synthesis of a peptide which is commonly employed in the pertinent art. More preferably, synthesis is carried out by a solution phase peptide synthesis, a solid-phase peptide synthesis, a fragment condensation method, or F-moc or T-BOC chemical method. Most preferably, synthesis is carried out by a solution phase peptide synthesis (Merrifield, RB., J. Am. Chem. Soc., 85, 2149, 1963), but it is not limited thereto.

The antimicrobial peptide of the present invention needs to satisfy the 3 requirements i) and ii), or the requirements i) and iii) that are described above. Specifically, the requirement i) is that the 1$^{st}$ to the 14$^{th}$ amino acids and the 31$^{st}$ to the 37$^{th}$ amino acids are all deleted, the requirement ii) is that glutamic acid (E), which is the 16$^{th}$ amino acid of the mother peptide of SEQ ID NO: 1, is substituted with lysine (K) as a basic amino acid having positive charge, and the requirement iii) is that glutamic acid (E) and aspartic acid (D), which are the 16$^{th}$ amino acid and the 26$^{th}$ amino acid of the mother peptide of SEQ ID NO: 1, respectively, are substituted with lysine (K) as a basic amino acid having positive charge.

The antimicrobial peptide of the present invention may preferably have the amino acid sequence of SEQ ID NO: 3 or SEQ ID NO: 5. Peptide having the amino acid sequence of SEQ ID NO: 3 is an antimicrobial peptide in which the 1$^{st}$ to the 14$^{th}$ amino acids and the 31$^{st}$ to the 37$^{th}$ amino acids are deleted from LL37 as a mother peptide and glutamic acid (E) as the 16$^{th}$ amino acid is substituted with lysine (K), and the peptide is named LL37-2. Peptide having the amino acid sequence of SEQ ID NO: 5 is an antimicrobial peptide in which the 1$^{st}$ to the 14$^{th}$ amino acids and the 31$^{st}$ to the 37$^{th}$ amino acids are deleted from LL37 as a mother peptide and glutamic acid (E) as the 16$^{th}$ amino acid and aspartic acid (D) as the 26$^{th}$ amino acid are substituted with lysine (K), and the peptide is named LL37-4.

The antimicrobial peptide is most preferably a peptide consisting of the amino acid sequence of SEQ ID NO: 3 and the amino acid sequence of SEQ ID NO: 5, but it is not limited thereto. According to utilization of increase/decrease of electric charge, the substitution can lower the cytotoxicity, and the substitution may be carried out to enhance or maintain the antimicrobial activity against Gram-negative bacteria and Gram-positive bacteria.

It is preferable that the antimicrobial peptide has an antimicrobial activity against Gram-positive bacteria, Gram-negative bacteria, or bacteria having tolerance to antibiotics, but it is not limited thereto.

Gram-positive bacteria are preferably every Gram-positive bacteria that are known in the pertinent art including Gram-positive bacteria of *Staphylococcus* sp., *Listeria* sp., *Corynebacterium* sp., *Lactobacillus* sp., and *Bacillus* sp. Gram-positive bacteria are more preferably Gram-positive bacteria of *Staphylococcus* sp. or *Listeria* sp. Gram-positive bacteria are most preferably *Staphylococcus aureus* or *Listeria monocytogenes*, but they are not limited thereto.

Gram-negative bacteria are preferably every Gram-negative bacteria that are known in the pertinent art including Gram-negative bacteria of *Acinetobacter* sp., *Pseudomonas* sp., *Escherichia* sp., *Salmonella* sp., *Leptospira* sp., and *Rickettsia* sp. Gram-negative bacteria are more preferably bacteria of *Acinetobacter* sp., *Pseudomonas* sp., *Escherichia* sp., or *Salmonella* sp. Gram-negative bacteria are most preferably *Acinetobacter baumannii*, *Escherichia coli*, *Pseudomonas aeruginosa*, or *Salmonella typhimurium*, but they are not limited thereto.

The bacteria having tolerance to antibiotics can be *Acinetobacter baumannii* which has tolerance to antibiotics, but they are not limited thereto.

Examples of the antibiotics include, although not limited thereto, aminoglycoside-based (aminoglycoside, gentamycin, neomycin, and the like), penicillin-based (ampicillin and the like), sulfonamide-based, beat-lactam based (beta-lactam, amoxicillin/clavulanic acid, and the like), chloramphenicol-based, erythromycin-based, florfenicol-based, fosfomycin-based, kanamycin-based, lincomycin-based, methicillin-based, quinolone-based, streptomycin-based, tetracycline-based, trimethoprim-based, and vancomycin-based antibiotics.

The antimicrobial peptide of the present invention may be a peptide which exhibits low cytotoxicity for cells derived from mouse or human.

The present invention further provides antibiotics comprising the aforementioned antimicrobial peptide as an effective component. The antimicrobial peptide is preferably a peptide having the amino acid sequence of SEQ ID NO: 3 or SEQ ID NO: 5, and each peptide is the same as described in the above.

Since LL37-2 (SEQ ID NO: 3) and LL37-4 (SEQ ID NO: 5) of the present invention, which are a homologue antimicrobial peptide derived from LL37 antimicrobial peptide, exhibit low cytotoxicity for cells derived from human while having a strong antimicrobial activity, the antimicrobial peptide of the present invention can be advantageously used as an effective component of antibacterial antibiotics.

For clinical administration, the peptide of the present invention can be administered parenterally, and it can be used in the form of a common pharmaceutical preparation. Parenteral administration may mean administration via a route other than oral administration like rectal, intravenous, intraperitoneal, intramuscular, intraarterial, transdermal, nasal, inhalational, intraocular, and subcutaneous administration. When the antimicrobial peptide of the present invention is used as a pharmaceutical product, one or more effective components exhibiting the same or similar activity may be additionally included.

Namely, the antimicrobial peptide of the present invention can be indeed administered as various parenteral preparations, and, in case of having a preparation, production is made by using a diluent or a vehicle such as filler, bulking agent, binding agent, moisturizing agent, disintegrating agent, or surfactant that are commonly used for producing a preparation. In a preparation for parenteral administration, a sterilized aqueous solution, a non-soluble preparation, a suspension, an oil preparation, a freeze-dried preparation, and a suppository are included. As a water insoluble solvent or a suspending solvent, propylene glycol, polyethylene glycol, or vegetable oil such as olive oil, and injectable ester such as ethylolate can be used. As a base for a suppository, WITEPSOL, macrogol, tween 61, cacao fat, laurin fat, glycerogelatin, or the like can be used.

Furthermore, the antimicrobial peptide of the present invention can be used after being admixed with various pharmaceutically acceptable carriers such as physiological saline or organic solvent. To enhance the stability or absorption property, carbohydrates such as glucose, sucrose, or dextran, antioxidants such as ascorbic acid or glutathione, chelating agents, low molecular weight proteins, or other stabilizers can be used as a pharmaceutical agent.

Effective dose of the antimicrobial peptide of the present invention is 0.1 to 2 mg/kg, and preferably 0.5 to 1 mg/kg. Administration can be made 1 to 3 times a day.

Total effective amount of the novel peptide of the present invention in the antibiotics of the present invention can be administered to a patient as a single dose in bolus form or infusion during a relatively short period of time, and it can be also administered according to a fractionated treatment protocol by which multiple dose is administered for a long period of time. With regard to the concentration described above, the effective dose is determined by considering not only the pharmaceutical administration route and number of treatment but also other various factors including age, health state, or the like of a patient. Thus, by considering them, a person having common knowledge in the pertinent art may determine suitable effective dose depending on specific use of the novel peptide of the present invention as antibiotics.

The present invention further provides an antibiotic cosmetic composition comprising the aforementioned antimicrobial peptide as an effective component.

The antimicrobial peptide is preferably a peptide having the amino acid sequence of SEQ ID NO: 3 or SEQ ID NO: 5, and it is the same as described above. This peptide exhibits low cytotoxicity for cells derived from human while showing a strong antimicrobial activity. As such, the antimicrobial peptide of the present invention can be advantageously used as an effective component of an antibiotic cosmetic composition.

In the cosmetic composition of the present invention, components commonly used for a cosmetic composition are included in addition to the antimicrobial peptide, and examples thereof include a common auxiliary agent such as an antioxidant, a stabilizing agent, a solubilizing agent, vitamin, a pigment, or a fragrance, and a carrier.

In the cosmetic composition of the present invention, the peptide of the present invention may be added in an amount of 0.1 to 50% by weight, and preferably 1 to 10% by weight to the cosmetic composition.

The cosmetic composition of the present invention may be produced in any formulation that is produced commonly in the pertinent art. For example, it can be produced as a formulation such as a solution, a suspension, an emulsion, paste, gel, cream, lotion, powder, a soap, a surfactant-containing cleanser, oil, powder foundation, emulsion foundation, wax foundation, or spray, but it is not limited thereto. More specifically, it can be produced as a formulation such as softening cosmetic water (skin water), nutritive cosmetic water (milk lotion), nutritive cream, massage cream, essence, eye cream, cleansing cream, cleansing foam, cleansing water, pack, spray, or powder.

When the formulation of the present invention is paste, cream, or gel, animal oil, vegetable oil, wax, paraffin, starch, tragacanth, cellulose derivatives, polyethylene glycol, silicone, bentonite, silica, talc, or zinc oxide can be used as a carrier component.

When the formulation of the present invention is powder or spray, lactose, talc, silica, aluminum hydroxide, calcium silicate, or polyamide powder can be used as a carrier component. When the formulation is spray, in particular, a propellant such as chlorofluorohydrocarbon, propane/butane, or dimethyl ether may be additionally included.

When the formulation of the present invention is a solution or an emulsion, a solvent, a solubilizing agent, or an emulsifying agent is used as a carrier component, and examples thereof include water, ethanol, isopropanol, ethyl carbonate, ethyl acetate, benzyl alcohol, benzyl benzoate, propylene glycol, 1,3-butyl glycol oil, glycerol aliphatic ester, polyethylene glycol, and fatty acid ester of sorbitan.

When the formulation of the present invention is a suspension, a liquid diluent such as water, ethanol, or propylene glycol, a suspending agent such as ethoxylated isostearyl alcohol, polyoxyethylene sorbitol ester, or polyoxyethylene sorbitan ester, microcrystalline cellulose, aluminum metahydroxide, bentonite, agar, or tragacanth can be used as a carrier component.

When the formulation of the present invention is a surfactant-containing cleanser, aliphatic alcohol sulfate, aliphatic alcohol ether sulfate, sulfosuccinic acid monoester, isethionate, imidazolinium derivatives, methyl taurate, sarcosinate, fatty acid amide ether sulfate, alkylamidobetaine, aliphatic alcohol, fatty acid glyceride, fatty acid diethanolamine, vegetable oil, lanolin derivatives, or ethoxylated glycerol fatty acid ester can be used as a carrier component.

The present invention further provides an antibiotic food additive comprising the aforementioned antimicrobial peptide as an effective component.

The antimicrobial peptide is preferably a peptide having the amino acid sequence of SEQ ID NO: 3 or SEQ ID NO: 5. This peptide exhibits low cytotoxicity for cells derived from human while showing a strong antimicrobial activity. As such, the antimicrobial peptide of the present invention can be advantageously used as an effective component of a food additive.

When the peptide of the present invention is used as a food additive, the peptide may be directly added or used with other food components, and it can be suitably used according to a general method. Blending amount of the effective component can be suitably determined depending on the purpose of use. In general, the peptide of the present invention is added in an amount of 15 parts by weight or less, and preferably 10 parts by weight or less relative to peptide raw materials. However, in case of application for a long period of time, the blending amount may be lower than the aforementioned range. As there is no problem in terms of the stability, the effective component may be used in an amount that is higher than the aforementioned range.

Type of the food is not particularly limited. Examples of the food to which the additive can be added include meat, sausage, bread, chocolate, candies, snacks, biscuits, pizza, ramen, other noodles, gums, dairy products including ice cream, various kinds of soup, beverage, tea, drink, alcohol beverage, and vitamin complex, and all foods in general sense are included therein.

The present invention further provides an antibiotic animal feed additive comprising the aforementioned antimicrobial peptide as an effective component.

The antimicrobial peptide is preferably a peptide having an amino acid sequence that is selected from a group consisting of the amino acid sequence of SEQ ID NO: 3 and the amino acid sequence of SEQ ID NO: 5, and it is the same as described above. This peptide exhibits low cytotoxicity for cells derived from human while showing a strong antimicrobial activity. As such, the antimicrobial peptide of the present invention can be advantageously used as an effective component of an animal feed additive.

The animal feed composition of the present invention has an effect of replacing existing antibiotics, inhibiting the growth of harmful pathogenic food bacteria to improve the health state of an animal, enhancing the body weight and meat quality of livestock, and enhancing the milk production amount and immunity of livestock. The animal feed composition of the present invention can be produced in the form of fermented animal feed, complete animal feed, pellets, silage, or the like.

The fermented animal feed can be produced by adding various microbes or enzymes other than the peptide of the present invention to ferment organic matters, and the complete animal feed can be produced by admixing the peptide of the present invention with various kinds of common animal feed. Animal feed in pellet form can be produced by applying heat and pressure to a complete feed in a pelletizing machine, and silage can be produced by fermenting forage with the microbes of the present invention. Fermented wet animal feed can be produced by, after collecting and transporting organic matters and admixing them with a vehicle at a certain ratio for moisture control and sterilization, fermenting organic matters like food waste at a temperature suitable for fermentation for 24 hours or longer to adjust moisture content to about 70%. Fermented dry animal feed can be produced according to adjustment of the moisture content to 30% to 40% or so by providing fermented wet animal feed additionally to a drying process. The present invention further provides a preservative composition, antibiotic biopesticides, and an antibiotic quasi-drug composition comprising the aforementioned antimicrobial peptide as an effective component.

The antimicrobial peptide is preferably a peptide having an amino acid sequence that is selected from a group consisting of the amino acid sequence of SEQ ID NO: 3 and the amino acid sequence of SEQ ID NO: 5, and it is the same as described above. This peptide exhibits low cytotoxicity for cells derived from human while showing a strong antimicrobial activity. As such, the antimicrobial peptide of the present invention can be advantageously used as an effective component of antibiotic biopesticides, a preservative composition, or an antibiotic quasi-drug composition.

Examples of the preservative composition include a cosmetics preservative and a pharmaceutical preservative. The preservative agent for food, cosmetics preservative, and pharmaceutical preservative are an additive which is used to prevent deterioration, degradation, discoloration, and chemical change of those products, and examples thereof include a sterilizer and an antioxidant. Also included are functional antibiotics having an activity of inhibiting growth or sterilizing degrading bacteria in food product and pharmaceutical product according to suppression of proliferation of microbes like bacteria, fungi, and yeast. As an ideal condition required for such preservative composition, the composition should not have any toxicity and should exhibit the effect even with a trace amount.

When the composition of the present invention is used as a quasi-drug additive, the antimicrobial peptide may be directly added or used with other quasi-drug or quasi-drug components, and it can be suitably used according to a general method. Blending amount of the effective component can be suitably determined depending on the purpose of use.

The quasi-drug composition of the present invention is preferably a sterilizing cleanser, a shower foam, a mouth wash, a water tissue, a liquid soap, a hand wash, a humidifier filler, a mask, an ointment, a patch, or a filter filler, although it is not limited thereto.

The present invention further provides a method for antimicrobial treatment in an individual including administering a pharmaceutically effective amount of the aforementioned antimicrobial peptide to an individual. The individual may be a mammal excluding human, but it is not limited thereto.

Hereinbelow, the present invention is explained in greater detail in view of the Examples. However, it is evident that the following Examples are given only for exemplification of the present invention and by no means the present invention is limited to the following Examples.

EXAMPLES

Example 1. Synthesis, Isolation, and Purification of Peptide

According to the solution phase peptide synthesis by Merrifield (Merrifield, R B., J. Am. Chem. Soc., 85:2149-2154, 1963), the inventors of the present invention carried out digestion of the $15^{th}$ to the $30^{th}$ amino acid residues of the amino acid sequence of LL37, which is a mother peptide described with the amino acid sequence of SEQ ID NO: 1. Resulting peptide composed of the 16 amino acids was named LL37-1 (SEQ ID NO: 2). Furthermore, after substituting the $2^{nd}$ amino acid of the amino acid sequence of LL37-1 with lysine (K), the resulting peptide was named LL37-2 (SEQ ID NO: 3), and, after substituting the $12^{th}$ amino acid of the amino acid sequence of LL37-1 with lysine (K), the resulting peptide was named LL37-3 (SEQ ID NO: 4). Still furthermore, after substituting in turn the $2^{nd}$ and $12^{th}$ amino acids of the amino acid sequence of LL37-1 with lysine (K), the resulting peptide was named LL37-4, and each of those peptides was synthesized accordingly.

Specifically, for the peptide in which the peptide designed in the present invention has a carboxy terminal in $NH_2$ form, a rink amide MBHA-resin was used as a starting material, and, for the peptide having a carboxy terminal in OH form, a Fmoc (9-fluorenylmethoxycarbonyl)-amino acid-Wang resin was used as a starting material.

Peptide chain extension based on Fmoc-amino acid coupling was carried out by DCC (N-hydroxybenzotrizole (HOBt)-dicyclo-hexycarbodiimide) method. After coupling Fmoc-amino acid at the terminal amino acid of each peptide, the Fmoc group is removed by using NMP (20% piperidine/N-methyl pyrrolidone) solution. Then, after washing several times with NMP and DCM (dichloromethane), drying with nitrogen gas was carried out. Then, a solution in which TFA (trifluoroacetic acid), phenol, thioanisole, $H_2O$, and triisopropylsilane are mixed at ratio of 85:5:5:2.5:2.5 (v/v) was added thereto followed by reaction for 2 to 3 hours to remove the protective group and separate the peptide from resin. Then, the peptide was allowed to precipitate in diethyl ether. The crude peptide obtained by the above method was purified by using a purification-type reverse phase (RP)-HPLC column (Delta Pak, C18 300 Å, 15, 19.0 mm×30 m, Waters, USA) based on acetonitrile gradient containing 0.05% TFA. The synthesized peptide was hydrolyzed with 6 N HCl at 110° C. Then, the resulting residues were concentrated under reduced pressure and dissolved in 0.02 N HCl. The amino acid composition was measured by using an amino acid analyzer (Hitachi 8500 A). To determine the purity and molecular weight of the peptide, MALDI mass analysis (Hill, et al., Rapid Commun. Mass Spectrometry, 5: 395, 1991) was carried out.

As a result, as shown in the following Table 1, the peptides represented by each amino acid described with SEQ ID NO: 1 to SEQ ID NO: 5 were synthesized with purity of 95% or higher, and the molecular weight was found to be the same as the expected molecular weight.

TABLE 1

Sequence, molecular weight, and retention time of peptides synthesized in the present invention

| Peptide name | Amino acid sequence | SEQ ID NO. | Retention time | Molecular weight (Da) |
|---|---|---|---|---|
| LL37 | LLGDFFRKSKEKIGKEFKRIV QRIKDFLRNLVPRTES-$NH_2$ | (SEQ ID NO. 1) | 38.433 | 4493.3 |
| LL37-1 | KEFKRIVQRIKDFLRN-$NH_2$ | (SEQ ID NO. 2) | 23.688 | 2089.7 |
| LL37-2 | KKFKRIVQRIKDFLRN-$NH_2$ | (SEQ ID NO. 3) | 21.554 | 2089.0 |
| LL37-3 | KEFKRIVQRIKKFLRN-$NH_2$ | (SEQ ID NO. 4) | 21.163 | 2101.8 |
| LL37-4 | KKFKRIVQRIKKFLRN-$NH_2$ | (SEQ ID NO. 5) | 19.436 | 2100.9 |

Example 2. Measurement of Antimicrobial Activity

To compare the antimicrobial activity among the peptides produced by the method of Example 1, the inventors of the present invention measured the minimal growth inhibitory concentration (MIC), which is minimum concentration of the peptide not allowing any dissociation of bacterial cells.

Specifically, the bacterial strains described in the following Table 2 were purchased and cultured to a mid-log phase in MHB (Mueller Hinton Broth) medium. Then, after dilution to bacterial cell concentration of $2 \times 10^5$ cells/50 μl, the cells were inoculated to a microtiter plate (NUNC, USA). Thereafter, LL37-1, LL37-2, LL37-3 or LL37-4 peptide which has been synthesized in Example 1 above was subjected to serial dilution, ½ times for each, in a 96-well plate.

After adding the peptides in an amount of 50 μl to the cell plate, the cells were cultured for 18 hours at 37° C. By using a microtiter plate reader (Merck Elisa reader, Germany), the absorbance was measured at a wavelength of 600 nm to determine the MIC value of each bacterial strain. As a control group, LL37 as a mother peptide was used and subjected to the same process as above to determine the MIC value of each strain.

TABLE 2

Bacterial strains used in the present invention and sources of the bacterial strains

| Category | Name of bacterial strain | Source | Accession number |
|---|---|---|---|
| Gram-positive bacteria | Staphylococcus aureus | American Type Culture Collection | ATCC 25923 |
|  | Listeria monocytogenes | Korean Collection for Type Cultures | KCTC 3710 |
| Gram-negative bacteria | Acinetobacter baumannii | Korean Collection for Type Cultures | KCTC 2508 |
|  | Escherichia coli | American Type Culture Collection | ATCC 25922 |
|  | Pseudomonas aeruginosa | American Type Culture Collection | ATCC 27853 |
|  | Salmonella typhimurium | Korean Collection for Type Cultures | KCTC 1925 |
| Bacteria having tolerance to antibiotics | Acinetobacter baumannii | Division of Infectious Diseases, Eulji University | Isolate 2 Isolate 3 Isolate 4 Isolate 5 Isolate 8 Isolate 9 Isolate 10 Isolate 11 Isolate 12 Isolate 13 Isolate 19 |

As a result, it was found that LL37-1, LL37-2, LL37-3 and LL37-4 peptides as a test group exhibit an antimicrobial activity for Gram-positive bacteria, Gram-negative bacteria, and antibiotic tolerant bacteria, as shown in the following Table 3. In particular, among the homologous peptides which have been synthesized, LL37-2 and LL37-4 were found to have an antimicrobial activity for antibiotic tolerant bacteria that is in similar level to LL37 as a mother peptide but they exhibit a higher antimicrobial activity for Gram-positive bacteria and Gram-negative bacteria than the mother peptide.

TABLE 3

Antimicrobial activity of antimicrobial peptides for Gram-positive bacteria, Gram-negative bacteria, and bacteria having tolerance to antibiotics

| Strain | | Peptide Minimal inhibitory concentration (μM) | | | | |
|---|---|---|---|---|---|---|
|  |  | LL37 | LL37-1 | LL37-2 | LL37-3 | LL37-4 |
| Gram-positive bacteria | S. aureus ATCC 25923 | 16 | 32 | 2 | 4 | 2 |
|  | L. monocytogenes KCTC 3710 | 64 | 128 | 16 | 64 | 16 |
| Gram-negative bacteria | A. baumannii KCTC 2508 | 2 | 16 | 4 | 16 | 4 |
|  | E. coli ATCC 25922 | 32 | 128 | 16 | 32 | 16 |
|  | P. aeruginosa ATCC 27853 | 8 | 16 | 8 | 8 | 4 |

TABLE 3-continued

Antimicrobial activity of antimicrobial peptides for Gram-positive bacteria, Gram-negative bacteria, and bacteria having tolerance to antibiotics

| Strain | | Peptide Minimal inhibitory concentration (μM) | | | | |
|---|---|---|---|---|---|---|
|  |  | LL37 | LL37-1 | LL37-2 | LL37-3 | LL37-4 |
|  | S. typhimurium KCTC 1925 | 32 | 32 | 4 | 8 | 4 |
| Bacteria having tolerance to antibiotics | A. baumannii #2 | 2 | 4 | 2 | 4 | 2 |
|  | A. baumannii #3 | 2 | 8 | 2 | 4 | 2 |
|  | A. baumannii #4 | 2 | 8 | 2 | 4 | 2 |
|  | A. baumannii #5 | 2 | 4 | 2 | 4 | 2 |
|  | A. baumannii #8 | 2 | 4 | 2 | 2 | 2 |
|  | A. baumannii #9 | 2 | 4 | 2 | 2 | 2 |
|  | A. baumannii #10 | 2 | 4 | 2 | 2 | 2 |
|  | A. baumannii #11 | 2 | 4 | 2 | 2 | 2 |
|  | A. baumannii #12 | 2 | 8 | 2 | 4 | 2 |
|  | A. baumannii #13 | 2 | 4 | 2 | 2 | 2 |
|  | A. baumannii #19 | 2 | 8 | 2 | 4 | 4 |

Example 3. Measurement of Antibiofilm Activity

To compare the antimicrobial activity among the peptides produced by the method of Example 1, the inventors of the present invention measured the biofilm inhibitory concentration value of the peptide for not allowing any dissociation of bacterial cells.

Specifically, among the bacterial strains described in the above Table 2, bacteria showing the most favorable biofilm forming were cultured to a mid-log phase in a medium with suitable composition. Then, after dilution to bacterial cell concentration of $1 \times 10^6$ cells/50 μl, the cells were inoculated to a microtiter plate. Thereafter, LL37, LL37-1, LL37-2, LL37-3 or LL37-4 peptide which has been synthesized in Example 1 above was diluted, 1/10 times for each, with 10 mM phosphate buffered physiological saline (PBS) in a 96-well plate. After adding the peptide (50 μl) to each well of the plate, the cells were cultured for 24 hours at 37° C. After removing the supernatant completely, the cells were fixed with 100% methanol for 15 minutes and stained for 1 hour with Crystal violet staining solution followed by rinsing for 3 times. Then, after dissolving in 95% ethanol, the absorbance was measured at a wavelength of 595 nm by using a microtiter plate reader to determine the biofilm minimal inhibitory concentration value of each bacterial strain.

As a result, as it is shown in the following Table 4, LL37-1, LL37-2, LL37-3 and LL37-4 peptides were found to exhibit a similar or stronger biofilm inhibitory activity in Acinetobacter baumannii compared to the mother peptide LL37 as a control.

TABLE 4

Antibiofilm activity of antimicrobial peptides for Gram-negative bacteria and bacteria having tolerance to antibiotics

| | | Peptide name Concentration, | Biofilm forming ability (%) | | | | |
|---|---|---|---|---|---|---|---|
| | | (μM) | 32 | 16 | 8 | 4 | 2 |
| Gram-negative bacteria | A. baumannii KCTC 2508 | LL37 | 10 | 23 | 33 | 39 | 42 |
| | | LL37-1 | 27 | 29 | 33 | 34 | 42 |
| | | LL37-2 | 23 | 22 | 28 | 34 | 37 |
| | | LL37-3 | 23 | 25 | 29 | 41 | 52 |
| | | LL37-4 | 22 | 23 | 28 | 32 | 48 |
| Bacteria having tolerance to antibiotics | A. baumannii #5 | LL37 | 15 | 36 | 40 | 74 | 97 |
| | | LL37-1 | 26 | 59 | 60 | 63 | 70 |
| | | LL37-2 | 18 | 19 | 67 | 69 | 95 |
| | | LL37-3 | 20 | 24 | 26 | 62 | 60 |
| | | LL37-4 | 20 | 22 | 49 | 59 | 74 |
| | A. baumannii #10 | LL37 | 13 | 53 | 54 | 58 | 62 |
| | | LL37-1 | 36 | 36 | 36 | 53 | 63 |
| | | LL37-2 | 28 | 29 | 29 | 33 | 39 |
| | | LL37-3 | 30 | 32 | 34 | 38 | 61 |
| | | LL37-4 | 30 | 33 | 33 | 37 | 49 |

Example 4. Measurement of Hemolytic Activity

To compare the cytotoxicity among the peptides that are produced by the method of Example 1, erythrocyte hemolytic activity of the synthesized peptide was measured.

Specifically, erythrocytes of a mouse (Balb/c, 6 week old, female) were diluted in PBS (pH 7.0) to have concentration of 8%, and then subjected to a treatment with LL37, LL37-1, LL37-2, LL37-3 or LL37-4, to have concentration of 1.56, 3.13, 6.25, 12.5, 25.0, 50.0 or 100.0 μM/well for each followed by a reaction for 1 hour at 37° C. After that, the amount of hemoglobin contained in a supernatant collected by centrifuge at 1,000×g was determined by measuring the absorbance at a wavelength of 414 nm. As a control group to be used as a reference for cell disruption level, the supernatant collected by a treatment with 1% Triton X-100 (Sigma, USA) and a reaction for 1 hour at 37° C. was used to measure the absorbance. By setting the resulting absorbance value at 100% of the hemolytic activity, hemolysis of each peptide was calculated using the following formula.

Erythrocyte disrupting ability (%)=(Absorbance A−Absorbance B)/(Absorbance C−Absorbance B)×100

(in the above formula, Absorbance A indicates the absorbance of a reaction solution treated with each peptide, in which the absorbance is measured at a wavelength of 414 nm; Absorbance B indicates the absorbance of a reaction solution treated with PBS, in which the absorbance is measured at a wavelength of 414 nm; and Absorbance C indicates the absorbance of a reaction solution treated with 1% Triton X-100, in which the absorbance is measured at a wavelength of 414 nm).

As a result, it was found as shown in Table 5 that, when mouse erythrocytes are treated with 100 μM LL37 peptide as a mother peptide, hemolysis of the mouse erythrocytes was yielded in an amount of 35%. On the other hand, LL37-1, LL37-2, LL37-3 or LL37-4 peptide did not exhibit any erythrocyte disrupting ability even at the concentration of 100 μM, and thus it was confirmed that the antimicrobial peptides of the present invention have less cytotoxicity than the mother peptide.

TABLE 5

Measurement of hemolytic activity of antimicrobial peptides

| Peptide name Concentration | Erythrocyte disrupting ability (%) | | | | | | |
|---|---|---|---|---|---|---|---|
| (μM) | 100 | 50 | 25 | 12.5 | 6.25 | 3.13 | 1.56 |
| LL37 | 35 | 8 | 3 | 2 | 1 | 1 | 1 |
| LL37-1 | 0 | 1 | 1 | 1 | 1 | 1 | 0 |
| LL37-2 | 1 | 1 | 1 | 1 | 1 | 0 | 0 |
| LL37-3 | 1 | 1 | 1 | 1 | 0 | 1 | 1 |
| LL37-4 | 1 | 1 | 1 | 0 | 1 | 1 | 1 |

Example 5. Determination of Cytotoxicity in Normal Cell Line

To determine the cytotoxicity of the peptides produced by the method of Example 1 in normal cell line, cytotoxicity was measured by using normal human keratinocyte cell line (HaCaT) and normal human fibroblast cell line (Hs27).

Specifically, normal human keratinocyte (HaCaT) cells and normal human fibroblast (Hs27) cells, which have been cultured in DMEM medium containing 10% FBS (fetal bovine serum), were aliquoted in a microtiter plate to have $1 \times 10^4$ cells per well. After culturing them for 24 hours, the cells were subjected to a treatment with LL37, LL37-1, LL37-2, LL37-3 or LL37-4 peptide, each at concentration of 0.5, 1, 2, 4, 8, 16 or 32 μM/well, followed by reaction for 24 hours in a 5% $CO_2$ incubator. After culture, a reaction solution containing 5 mg/ml MTT (Thiazolyl Blue Tetrazolium Bromide) dissolved in phosphate buffered saline (PBS) was added in an amount of 10 μl to each well and the reaction was allowed to occur for 1 hour. After that, the supernatant was discarded, and, by dissolving MTT crystals that are formed by adding 200 μl DMSO (dimethyl sulfoxide), the absorbance at 570 nm was measured to determine the cell survival ability.

As a result, it was found as shown in the following Table 6 that, when the cells are treated with LL37 as a mother peptide (32 μM), HaCaT cells and Hs27 cells showed the cell survival ability of 17% and 19%, respectively, indicating that LL37 peptide exhibits very high cytotoxicity. On the other hand, when treated with LL37-1, LL37-2, LL37-3 or LL37-4 peptides at a concentration of 32 μM, HaCaT cells exhibited the cell survival ability of 104%, 107%, 104% and 101%, respectively, and Hs27 cells exhibited the cell survival ability of 95%, 97%, 95% and 93%, respectively, indicating that LL37-1, LL37-2, LL37-3 and LL37-4 peptides hardly exhibit any cytotoxicity compared to the mother peptide.

TABLE 6

Analysis of cytotoxicity of antimicrobial peptides

| | Peptide name Concentration, | Cell survival ability (%) | | | | | | |
|---|---|---|---|---|---|---|---|---|
| | (μM) | 32 | 16 | 8 | 4 | 2 | 1 | 0.5 |
| HaCaT | LL37 | 17 | 83 | 99 | 98 | 96 | 99 | 99 |
| | LL37-1 | 104 | 101 | 103 | 99 | 98 | 103 | 97 |
| | LL37-2 | 107 | 107 | 101 | 102 | 104 | 106 | 100 |
| | LL37-3 | 104 | 104 | 98 | 98 | 101 | 100 | 96 |
| | LL37-4 | 101 | 94 | 92 | 96 | 97 | 103 | 100 |
| Hs27 | LL37 | 19 | 82 | 90 | 89 | 90 | 90 | 95 |
| | LL37-1 | 95 | 92 | 96 | 95 | 103 | 100 | 100 |
| | LL37-2 | 97 | 93 | 89 | 91 | 94 | 92 | 92 |

TABLE 6-continued

Analysis of cytotoxicity of antimicrobial peptides

| Peptide name Concentration, | Cell survival ability (%) | | | | | | |
|---|---|---|---|---|---|---|---|
| (µM) | 32 | 16 | 8 | 4 | 2 | 1 | 0.5 |
| LL37-3 | 95 | 93 | 91 | 90 | 93 | 92 | 94 |
| LL37-4 | 93 | 96 | 93 | 90 | 97 | 94 | 94 |

Example 6. Determination of Antimicrobial Activity of Peptides at Ion Concentration of Living Body To determine the antimicrobial activity of peptides prepared by the method of above Example 1 in the presence of different ions in living body, minimal inhibitory concentration (MIC), i.e., lowest concentration of a peptide not allowing bacterial cell division, was measured.

Specifically, among the bacterial strains that are described in the above Table 2, *Acinetobacter baumannii* KCTC 2508 cells were cultured to a mid-log phase in MHB (Mueller Hinton Broth) medium, and, after diluting LL37-2 or LL37-4 peptide synthesized in the above Example 1 in a solution containing different kind of ions (sodium chloride, calcium chloride, magnesium chloride, and iron chloride) at different concentration, it was added to the plate in an amount of 50 µl per plate. After that, the cultured cells were diluted to cell concentration of 2×10⁵ cells/50 µl, inoculated to a microtiter plate (NUNC, USA), and then cultured again for 18 hours at 37° C. By using a microtiter plate reader (Merck Elisa reader, Germany), absorbance at wavelength of 600 nm was measured and MIC value was determined for each strain. As a control, the MIC values of LL37, LL37-2 and LL37-4 for *Acinetobacter baumannii* KCTC 2508, which are shown in the above Table 3, were used.

As a result, it was found that, except for sodium chloride for generating monovalent ions, LL37-2 and LL37-4 peptides exhibit the similar antimicrobial activity for *Acinetobacter baumannii* compared to the control MIC value, as shown in the following Table 7.

cells were cultured to a mid-log phase in MHB medium, and, after diluting the cells to a cell concentration of 2×10⁵ cells/10 ml, the cells were admixed with agarose which has been adjusted to final concentration of 1% and then evenly spread and solidified on a Petri dish. After that, the peptide adjusted to a concentration of 100 µg/ml was admixed with 10.7 nM trypsin and reacted for 10 minutes at 37° C. After applying a paper disk (diameter: 6 mm) on the solidified Petri dish, the peptide obtained after the reaction with trypsin was aliquoted thereto in an amount of 25 µl. After culture for 18 hours at 37° C., diameter of the clear zone around the paper disk was measured so that the level of antimicrobial activity for *Acinetobacter baumannii* KCTC 2508 was determined.

As a result, as shown in FIG. 1, while LL37 as a mother peptide was completely degraded by trypsin and did not exhibit any antimicrobial activity, LL37-2 and LL37-4 peptides showed the antimicrobial activity of the peptides for *Acinetobacter baumannii* KCTC 2508, even though there was a decrease in clear zone when the cells are treated with trypsin protease. i.e., decrease of 1.75 mm for each compared to no treatment with trypsin.

Example 8. Measurement of Circular Dichroism Spectrum

To determine whether or not an α-helical structure as a secondary structure is induced by the peptides produced by the method of Example 1, measurement was carried out using circular dichroism.

Specifically, LL37, LL37-1, LL37-2, LL37-3 or LL37-4 peptide was added at a concentration of 40 µM to phosphate buffered saline, 50% 2,2,2-trifluoroethanol (TFE), or 30 mM sodium dodecyl sulfate (SDS) solution. After adding the mixture to a cell with 0.1 cm path length, the temperature was set at 25° C. and a circular dichroism spectrum was measured by using Jasco 810 spectrophotometer. As a formula to calculate an α-helical structure for the above circular dichroism spectrum, the following formula was used.

$$[\theta] = \frac{\theta_{obs}}{10 \cdot l \cdot c}$$

TABLE 7

Antimicrobial activity of antimicrobial peptides for *Acinetobacter baumannii* KCTC 2508 at different ion types and different ion concentrations

| | Minimal inhibitory concentration of antimicrobial peptide (µM) | | | | | | | | | | | |
|---|---|---|---|---|---|---|---|---|---|---|---|---|
| | | Sodium chloride (mM) | | | Calcium chloride (mM) | | | Magnesium chloride (mM) | | | Iron chloride (mM) | |
| | Control | 50 | 100 | 150 | 1.25 | 2.5 | 5 | 0.5 | 1 | 2 | 2 | 4 | 8 |
| LL37 | 2 | 4 | 4 | 8 | 2 | 2 | 2 | 4 | 4 | 4 | 2 | 4 | 4 |
| LL37-2 | 4 | 8 | 16 | 32 | 4 | 4 | 8 | 4 | 4 | 4 | 4 | 4 | 4 |
| LL37-4 | 4 | 8 | 16 | 32 | 4 | 4 | 8 | 4 | 4 | 4 | 4 | 4 | 4 |

Example 7. Determination of Peptide Stability Against Trypsin

To determine the activity of the peptides, which have been prepared by the method of Example 1, in the presence of trypsin as one type of proteases, peptide stability against protease was determined by radial diffusion assay.

Specifically, among the bacterial strains that are described in the above Table 2, *Acinetobacter baumannii* KCTC 2508

(in the formula, $\theta_{obs}$ represents the millidegrees of a signal; l represents the optical path-length of a cell (cm); and c represents the concentration of added peptide (mol/l)).

Figure 2:
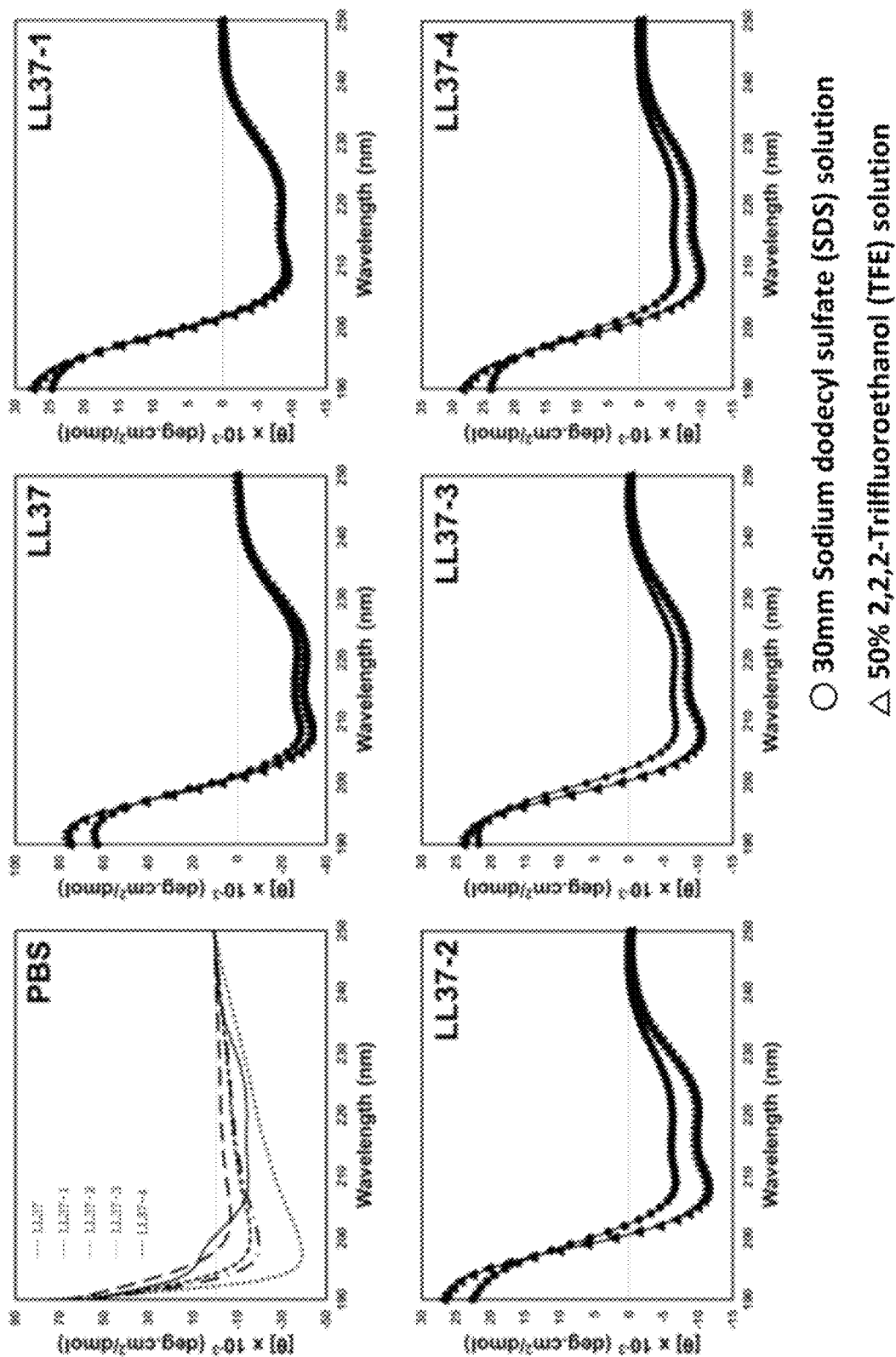
FIG. 2 shows the result of determining forming of, in various solvents, a secondary structure by LL37 (control) as a mother antimicrobial peptide and LL37-1, LL37-2, LL37-3 and LL37-4, which are a LL37 homologous novel peptide.

As a result, no secondary structure was formed when each peptide was added to the phosphate buffered saline, as it is shown in FIG. 2. However, when each peptide was added to 50% TFE solution or 30 mM SDS solution, it was found that the α-helical structure. i.e., a secondary structure, was formed with every peptide, although there was a variation in the forming degree. Based on the above results, it was realized that, in a SDS solution and a TFE solution that are similar to a membrane of bacteria as microorganism, an α-helical structure is formed by the antimicrobial peptides of the present invention.

Example 9. Flow Cytometry Measurement

To determine whether or not the peptides prepared by the method of Example 1 have any effect on bacteria membrane, an analysis was made by flow cytometry.

Specifically, *Acinetobacter baumannii* KCTC 2508 strain was treated with LL37 or LL37-1, LL37-2, LL37-3 and LL37-4 (at concentration of MIC), and then the reaction was allowed to occur for 30 minutes at 37° C. After that, the supernatant was removed by centrifuge (10,000 rpm) and stained with propidium iodide (PI, concentration of 10 μg/ml) for 30 minutes at 4° C. Thereafter, unbound propidium iodide was removed by centrifuge, and the problem of cell aggregation phenomenon was solved by adding physiological saline (PBS) in an amount of 1 ml. Then, by using Bechman flow cytometry, the effect of the peptides exhibited on bacteria membrane was determined.

Figure 3:
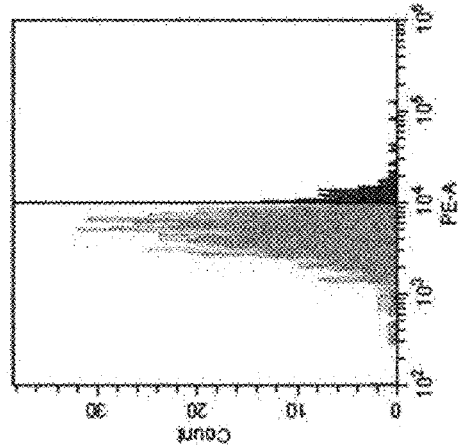
FIG. 3 shows the result of determining the influence of LL37 (control) as a mother antimicrobial peptide and LL37-1, LL37-2, LL37-3 and LL37-4, which are a LL37 homologous novel peptide, on bacteria membrane of *Acinetobacter baumannii* KCTC 2508 strain, in which the determination was made by flow cytometry after treatment of the strain with each peptide followed by PI staining.
Figure 3:
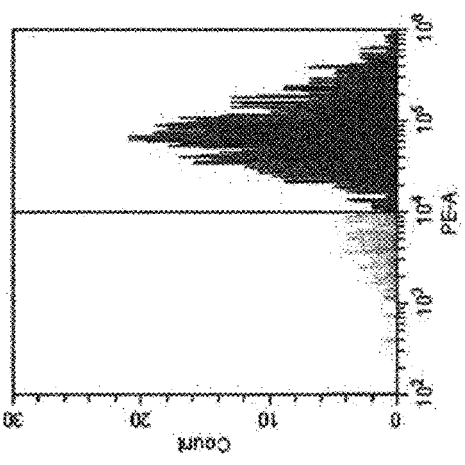
Figure 3:
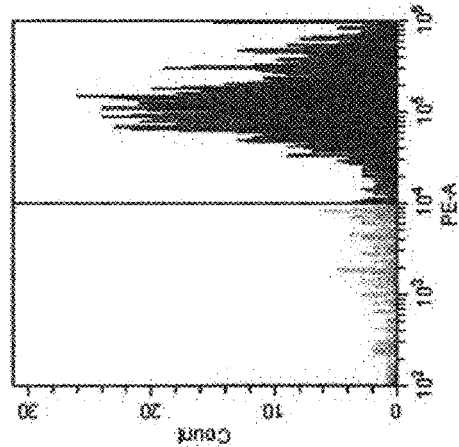
Figure 3:
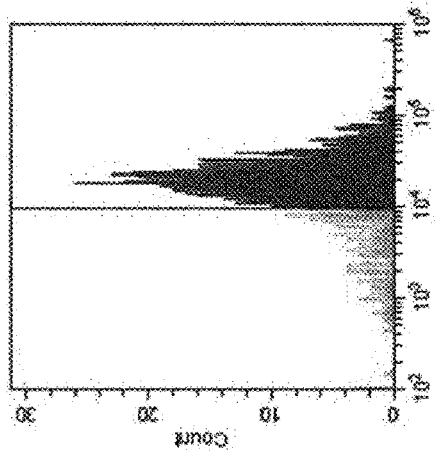
Figure 3:
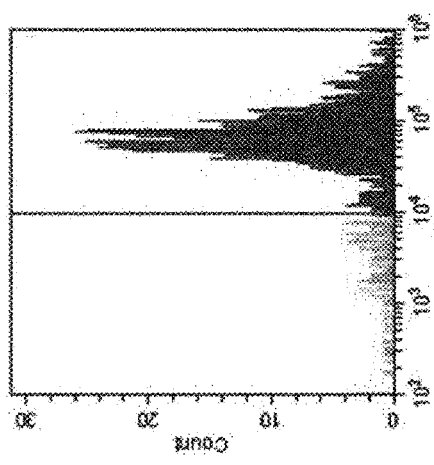
Figure 3:
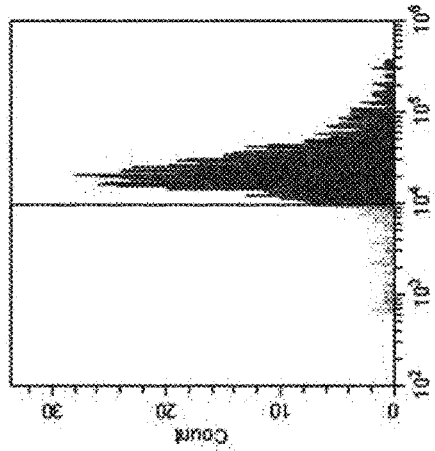

As a result, the bacteria membrane was damaged by LL37-1, LL37-2, LL37-3 and LL37-4 including LL37 as a mother peptide, thus yielding the rightward shift of fluorescence signal as shown in FIG. 3.

Example 10. Analysis of Effect of Antimicrobial Peptides on *Acinetobacter baumannii*

To specifically determine the degree of antimicrobial activity of the synthesized peptides of the present invention, the influence of mother peptide LL37 and homologous peptides LL37-1, LL37-2, LL37-3 and LL37-4 on bacteria membrane, i.e., membrane-disrupting property, was determined by low vacuum scanning electron microscopy.

Specifically, *Acinetobacter baumannii* KCTC 2508 cells were cultured to a mid-log phase in MHB medium, and then diluted to a cell concentration of $2 \times 10^7$ cells/ml in physiological saline containing 10% MHB medium. The diluted cells were treated with LL37 or LL37-1 to LL37-4 peptides as a comparative group, each at MIC concentration, and reacted for 30 minutes at 37° C. After that, by using 2.5% glutaraldehyde, the bacterial cells were fixed for 30 minutes at room temperature and then for 12 hours at 4° C. After carrying out washing with buffer, the cells were fixed again with osmium tetrachloride (0504) and dehydrated in stepwise manner by using ethanol. After the dehydration, platinum coating was carried out and the cells were observed by low vacuum scanning electron microscopy.

Figure 4:
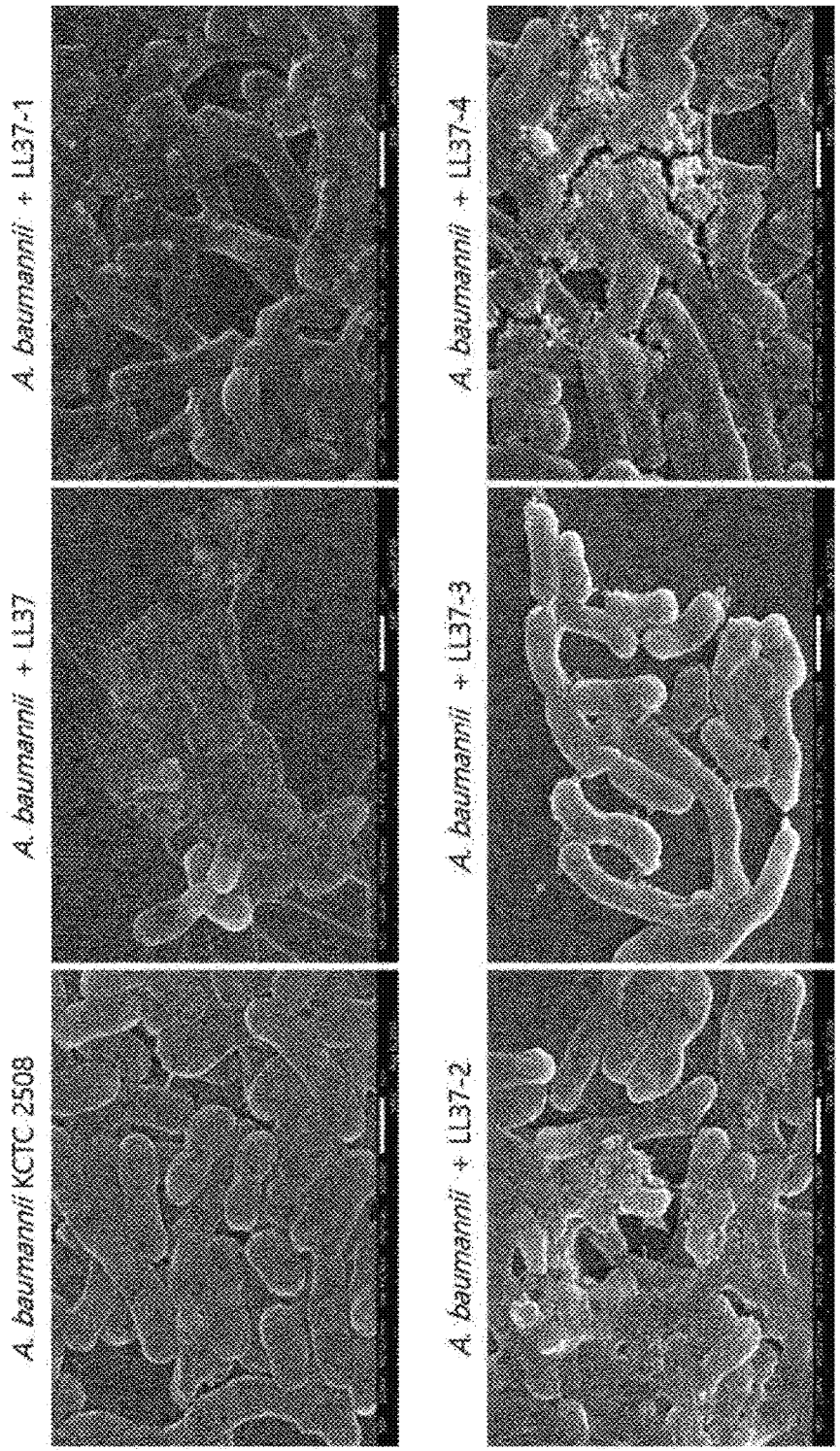
FIG. 4 shows the result of determining the bacteria membrane-disrupting property of LL37 as a control antimicrobial peptide and LL37-1, LL37-2, LL37-3 or LL37-4 which are a test group antimicrobial peptide, in which disruption of the membrane of *Acinetobacter baumannii* was examined by low vacuum scanning electron microscopy.

As a result, as it is shown in FIG. 4, it was able to observe that the mother peptide LL37 and also LL37-1, LL37-2, LL37-3 and LL37-4 peptides act on the cellular membrane of *Acinetobacter baumannii* to yield disruption of bacteria membrane. In particular, with LL37-2 and LL37-4 which have been found above to have an excellent antimicrobial activity, the cellular membrane of *Acinetobacter baumannii* was disrupted more compared to LL37-1 and LL37-3.

Example 11. Determination of Change in Expression of Inflammatory Cytokines Caused by Peptides To see whether or not a change in expression of inflammatory cytokines in macrophage is caused by the peptides that are prepared by the method of above Example 1, determination was made by Western blot and real time reverse transcription polymerase chain reaction.

Specifically, *Acinetobacter baumannii* KCTC 2508 cells were cultured to a mid-log phase in MHB medium, and then diluted to a cell concentration of $1 \times 10^7$ cells/ml in physiological saline. Human macrophage cells (U937) were then infected with the resulting cells in time-dependent manner to yield the first sample, and another macrophage cells were infected with *Acinetobacter baumannii* KCTC 2508 cells, which have been diluted to a concentration of $1 \times 10^7$ cells, and added with, 1 hour after the infection, mother peptide LL37 or the homologous peptide to collect the second sample after 9 hours. Both collected samples were treated with cell lysis buffer to obtain the supernatant (sup) and pellet (lysate). Thereafter, by Western blot and real time reverse transcription polymerase chain reaction, a change in the expression level of inflammatory cytokines was examined.

Figure 5:
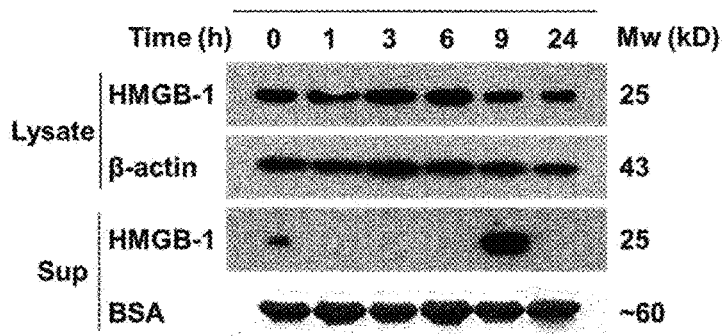
FIG. 5 shows the result of determining the expression level of inflammatory cytokines according to addition of LL37 (control) as a mother antimicrobial peptide or LL37-1, LL37-2, LL37-3 and LL37-4, which are a LL37 homologous novel peptide, in which the determination was made by Western blot and real time reverse transcription polymerase chain reaction after infection with *Acinetobacter baumannii*. In the figure, 'lysate' represents the pellet and 'sup' represents the supernatant.
Figure 5:
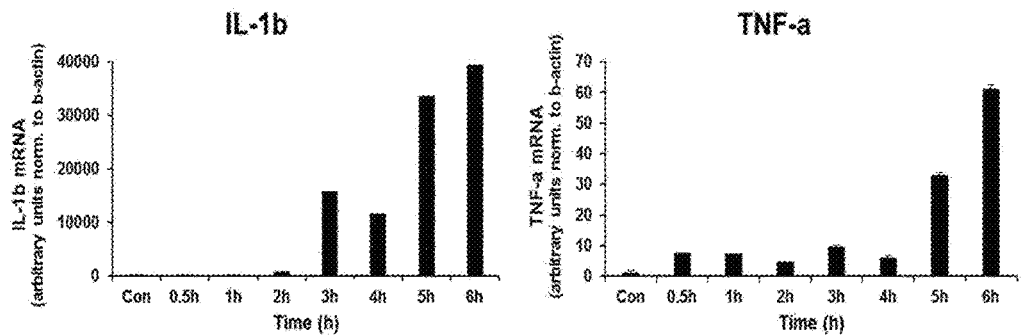
Figure 5:
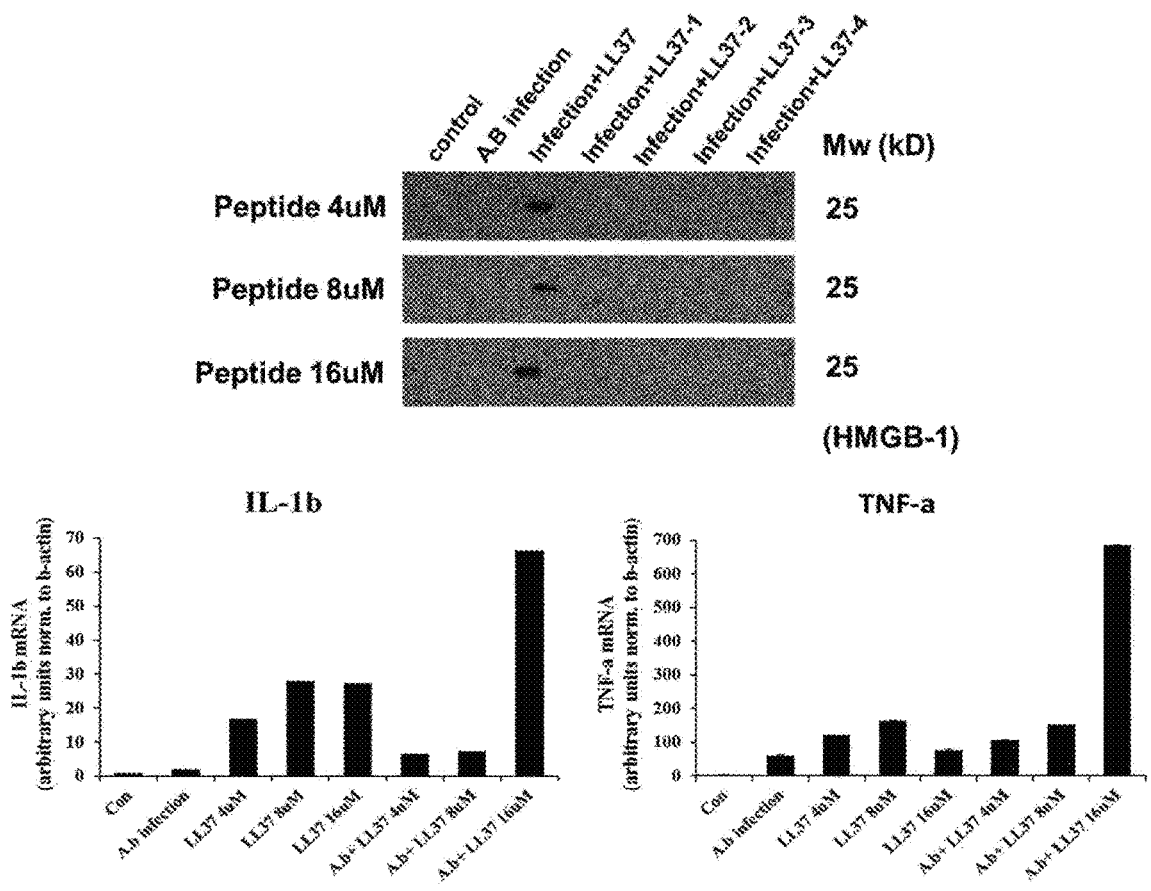

As a result, as it is shown FIG. 5, when human macrophage cells were infected with *Acinetobacter baumannii* KCTC 2508, it was found that HMGB-1 (High Mobility Group Box 1) and late cytokine (IL-1b and TNF-α) have increased at the hour 9 range. In case of adding each of the homologous peptides LL37-1, LL37-2, LL37-3 and LL37-4, it was found that the increase in expression level of HMGB-1 and late cytokine is lower. However, in case of the treatment with mother peptide LL37, the expression of the inflammatory cytokines has increased more in conditions with symptoms.

Hereinbelow, Production examples for producing the composition of the present invention are exemplified.

<Production Example 1> Production of Pharmaceutical Preparation

<1-1> Production of Powder Preparation

| Peptide of the present invention | 20 mg |
| Lactose | 20 mg |

After mixing the above components, a powder preparation was produced by filling them in a sealed pack.

<1-2> Production of Tablet

| Peptide of the present invention | 10 mg |
| Corn starch | 100 mg |
| Lactose | 100 mg |
| Magnesium stearate | 2 mg |

After mixing the above components, a tablet was produced according to tabletting by a common method for producing a tablet.

<1-3> Production of Capsule Preparation

| Peptide of the present invention | 10 mg |
| Crystalline cellulose | 3 mg |
| Lactose | 14.8 mg |
| Magnesium stearate | 0.2 mg |

After mixing the above components, a capsule preparation was produced according to filling them in a gelatin capsule by a common method for producing a capsule preparation.

<1-4> Production of Liquid Preparation

| Peptide of the present invention | 20 mg |
|---|---|
| High fructose corn syrup | 10 g |
| Mannitol | 5 g |
| Purified water | suitable amount |

According to a common method for producing a liquid preparation, each component was added to purified water for dissolution. After adding a suitable amount of lemon flavor, the above components were admixed with one another followed by addition of purified water to adjust the entire volume to 100 ml. The mixture was then filled in a brown bottle followed by sterilization to produce a liquid preparation.

<1-5> Production of Injection Solution

| Peptide of the present invention | 10 µg/ml |
|---|---|
| Dil. hydrochloric acid BP | till to have pH 7.6 |
| Sodium chloride BP for injection | 1 ml at maximum |

In sodium chloride BP for injection with suitable volume, the peptide of the present invention was dissolved. pH of the resulting solution was adjusted to pH 7.6 by using dil. hydrochloric acid BP, and the volume was adjusted by using sodium chloride BP for injection followed by thorough mixing. The resulting solution was filled in a 5 ml Type I ampoule made of transparent glass. By melting the glass, the ampoule was sealed while having air in the top. Then, according to autoclave for 15 minutes or longer at 120° C., sterilization was carried out to produce an injection solution.

<Production Example 2> Production of Cosmetics

<2-1> Softening Cosmetic Water (Skin Lotion)

To produce a softening cosmetic water containing the peptide of the present invention, blending can be carried out as described in the following Table 8 and production can be made according to a common production method in the cosmetic field.

TABLE 8

Softening cosmetic water composition

| Component | Content (% by weight) |
|---|---|
| Peptide of the present invention | 0.1 to 30 |
| 1,3-Butylene glycol | 3.0 |
| Glycerin | 5.0 |
| Polyoxyethylene (60) hydrogenated castor oil | 0.2 |
| Ethanol | 8.0 |
| Citric acid | 0.02 |
| Sodium citrate | 0.06 |
| Preservative | trace amount |
| Fragrance | trace amount |
| Purified water | To 100 |

<2-2> Nutritive Cosmetic Water (Lotion)

To produce an antimicrobial nutritive cosmetic water containing the peptide of the present invention, blending can be carried out as described in the following Table 9 and production can be made according to a common production method in the cosmetic field.

TABLE 9

Nutritive cosmetic water composition

| Component | Content (% by weight) |
|---|---|
| Peptide of the present invention | 0.1 to 30 |
| Squalane | 10.0 |
| Monooleic acid polyoxyethylene sorbitan | 2.0 |
| Lignum vitae oil | 0.1 to 30 |
| 1,3-Butylene glycol | 8.0 |
| Glycerin | 5.0 |
| Polyoxyethylene (60) hydrogenated castor oil | 0.2 |
| Ethanol | 8.0 |
| Citric acid | 0.02 |
| Sodium citrate | 0.06 |
| Preservative | trace amount |
| Fragrance | trace amount |
| Purified water | To 100 |

<2-3> Essence

To produce an antimicrobial essence containing the peptide of the present invention, blending can be carried out as described in the following Table 10 and production can be made according to a common production method in the cosmetic field.

TABLE 10

Essence composition

| Component | Content (% by weight) |
|---|---|
| Peptide of the present invention | 0.1 to 30 |
| Sitosterol | 1.7 |
| Polyglyceryl 2-oleate | 1.5 |
| Ceramide | 0.7 |
| Ceteareth-4 | 1.2 |
| Cholesterol | 1.5 |
| Dicetyl phosphate | 0.4 |
| Conc. glycerin | 5.0 |
| Carboxyvinyl polymer | 0.2 |
| Xanthan gum | 0.2 |
| Preservative | trace amount |
| Fragrance | trace amount |
| Purified water | To 100 |

<2-4> Facial Cleanser (Cleansing Foam)

To produce an antimicrobial facial cleanser (cleansing foam) containing the peptide of the present invention, blending can be carried out as described in the following Table 11 and production can be made according to a common production method in the cosmetic field.

TABLE 11

Facial cleanser composition

| Component | Content (% by weight) |
|---|---|
| Peptide of the present invention | 0.1 to 30 |
| Sodium N-acylglutamate | 20.0 |
| Glycerin | 10.0 |
| PEG-400 | 15.0 |
| Propylene glycol | 10.0 |
| POE (15) oleyl alcohol ether | 3.0 |
| Laurin derivatives | 2.0 |
| Methyl paraben | 0.2 |
| EDTA-4Na | 0.03 |
| Fragrance | 0.2 |
| Purified water | To 100 |

<2-5> Nutritive Cream

To produce an antimicrobial nutritive cream containing the peptide of the present invention, as described in the following Table 12, production can be made according to a common production method in the cosmetic field.

TABLE 12

Nutritive cream composition

| Component | Content (% by weight) |
|---|---|
| Peptide of the present invention | 0.1 to 30 |
| Vaseline | 7.0 |
| Fluid paraffin | 10.0 |
| Bees wax | 2.0 |
| Polysorbate 60 | 2.5 |
| Sorbitan sesquioleate | 1.5 |
| Squalane | 3.0 |
| Propylene glycol | 6.0 |
| Glycerin | 4.0 |
| Triethanolamine | 0.5 |
| Xanthan gum | 0.5 |
| Tocopheryl acetate | 0.1 |
| Fragrance, preservative | trace amount |
| Purified water | To 100 |

<2-6> Massage Cream

To produce an antimicrobial massage cream containing the peptide of the present invention, as described in the following Table 13, production can be made according to a common production method in the cosmetic field.

TABLE 13

Massage cream composition

| Component | Content (% by weight) |
|---|---|
| Peptide of the present invention | 0.1 to 30 |
| Propylene glycol | 6.0 |
| Glycerin | 4.0 |
| Triethanolamine | 0.5 |
| Bees wax | 2.0 |
| Tocopheryl acetate | 0.1 |
| Polysorbate 60 | 3.0 |
| Sorbitan sesquioleate | 2.5 |
| Cetaryl alcohol | 2.0 |
| Fluid paraffin | 30.0 |
| Xanthan gum | 0.5 |

TABLE 13-continued

Massage cream composition

| Component | Content (% by weight) |
|---|---|
| Fragrance, preservative | trace amount |
| Purified water | To 100 |

<2-7> Pack

To produce an antimicrobial pack containing the peptide of the present invention, as described in the following Table 14, production can be made according to a common production method in the cosmetic field.

TABLE 14

Pack composition

| Component | Content (% by weight) |
|---|---|
| Peptide of the present invention | 0.1 to 30 |
| Propylene glycol | 2.0 |
| Glycerin | 4.0 |
| Polyvinyl alcohol | 10.0 |
| Ethanol | 7.0 |
| PEG-40 (Hydrogenated castor oil) | 0.8 |
| Triethanolamine | 0.3 |
| Fragrance, preservative | trace amount |
| Purified water | To 100 |

The present invention is not limited to Examples and Production examples that are described above and various modifications and changes can be made by a person skilled in the art. Also, an application can be made to cosmetics of various usages including color cosmetics. Furthermore, depending on the effect, use can be made for a pharmaceutical preparation which can be applied to human body by thin coating, i.e., ointment, and it is included in the spirit and scope of the present invention that is defined by the attached claims.

A sequence listing electronically submitted with the present application on Sep. 4, 2020 as an ASCII text file named 20200904_Q36820GR10_TU_SEQ, created on Aug. 31, 2020 and having a size of 2000 bytes, is incorporated herein by reference in its entirety.

What is claimed is:

1. A method for antimicrobial treatment in a subject, the method comprising administering a composition comprising a pharmaceutically effective amount of an antimicrobial peptide in which, in the amino acid sequence of SEQ ID NO: 1, (i) the $1^{st}$ to the $14^{th}$ amino acids and the $31^{st}$ to the $37^{th}$ amino acids are deleted, and (ii) the $16^{th}$ amino acid is substituted with lysine (K), or $16^{th}$ and the $26^{th}$ amino acids are substituted with lysine (K).

2. The method of claim 1, wherein the antimicrobial peptide consists of the amino acid sequence of SEQ ID NO: 3.

3. The method of claim 1, wherein the antimicrobial treatment is against Gram-positive bacteria, Gram-negative bacteria, or bacteria having tolerance to antibiotics.

4. The method of claim 3, wherein the Gram-positive bacteria are *Staphylococcus aureus* or *Listeria monocytogenes*.

5. The method of claim 3, wherein the Gram-negative bacteria are *Acinetobacter baumannii*, *Escherichia coli*, *Pseudomonas aeruginosa*, or *Salmonella typhimurium*.

6. The method of claim 3, wherein the bacteria having tolerance to antibiotics are *Acinetobacter baumannii* which has tolerance to antibiotics.

7. The method of claim 1, wherein the antimicrobial peptide consists of the amino acid sequence of SEQ ID NO: 5.

* * * * *